(12) United States Patent
Jones et al.

(10) Patent No.: US 7,357,809 B2
(45) Date of Patent: Apr. 15, 2008

(54) CHEMICALLY BASED VASCULAR OCCLUSION DEVICE DEPLOYMENT WITH GRIPPING FEATURE

(75) Inventors: Donald K. Jones, Lauderhill, FL (US); Vladimir Mitelberg, Aventura, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 241 days.

(21) Appl. No.: 11/171,896

(22) Filed: Jun. 30, 2005

(65) Prior Publication Data

US 2007/0005098 A1  Jan. 4, 2007

(51) Int. Cl.
*A61B 17/00* (2006.01)
(52) U.S. Cl. ...................................... 606/205
(58) Field of Classification Search ................ 606/200, 606/108; 92/89, 90, 91, 92, 93
See application file for complete search history.

(56) References Cited

U.S. PATENT DOCUMENTS

| | | | |
|---|---|---|---|
| 5,002,556 A | | 3/1991 | Ishida et al. |
| 5,108,407 A | | 4/1992 | Geremia et al. |
| 5,609,608 A | | 3/1997 | Benett et al. |
| 5,637,087 A | * | 6/1997 | O'Neil et al. ................. 604/82 |
| 5,989,242 A | | 11/1999 | Saadat et al. |
| 6,063,100 A | | 5/2000 | Diaz et al. |
| 6,068,644 A | | 5/2000 | Lulo et al. |
| 6,238,415 B1 | | 5/2001 | Sepetka et al. |
| 6,277,125 B1 | | 8/2001 | Barry et al. |
| 6,361,547 B1 | * | 3/2002 | Hieshima ..................... 606/200 |
| 6,478,773 B1 | | 11/2002 | Gandhi et al. |
| 6,494,884 B2 | | 12/2002 | Gifford, III et al. |
| 6,641,576 B1 | | 11/2003 | Vito et al. |
| 6,689,141 B2 | | 2/2004 | Ferrera et al. |
| 6,743,236 B2 | | 6/2004 | Barry et al. |
| 6,871,594 B1 | | 3/2005 | Estrella |
| 2003/0220666 A1 | | 11/2003 | Mirigian et al. |
| 2004/0153025 A1 | | 8/2004 | Seifert et al. |
| 2004/0218966 A1 | | 11/2004 | Fuller |
| 2004/0225279 A1 | | 11/2004 | Raymond |

FOREIGN PATENT DOCUMENTS

EP          1537838       6/2005
WO    WO 92/09651       6/1992

OTHER PUBLICATIONS

European Search Report in EP 06 25 3235, dated Oct. 24, 2006.

\* cited by examiner

*Primary Examiner*—Michael J. Hayes
*Assistant Examiner*—Christina Gettman
(74) *Attorney, Agent, or Firm*—Michael W. Montgomery

(57) ABSTRACT

A vascular occlusion device deployment system for placing an occlusion device at a preselected site within the vasculature of a patient. The deployment system employs a pusher including a gripper located at the distal end of the pusher to releasably retain a vascular occlusion device. The gripper is expanded by an expandable chemical reaction chamber so that the gripper releases the vascular occlusion device, thereby deploying the vascular occlusion device.

21 Claims, 2 Drawing Sheets

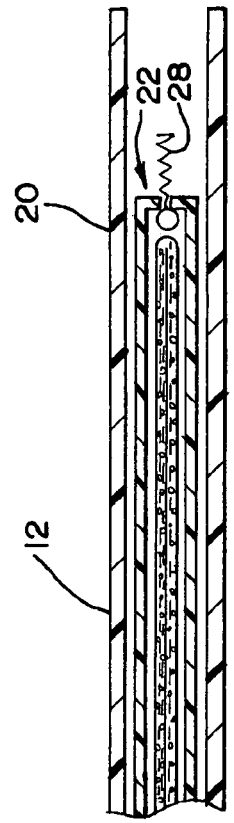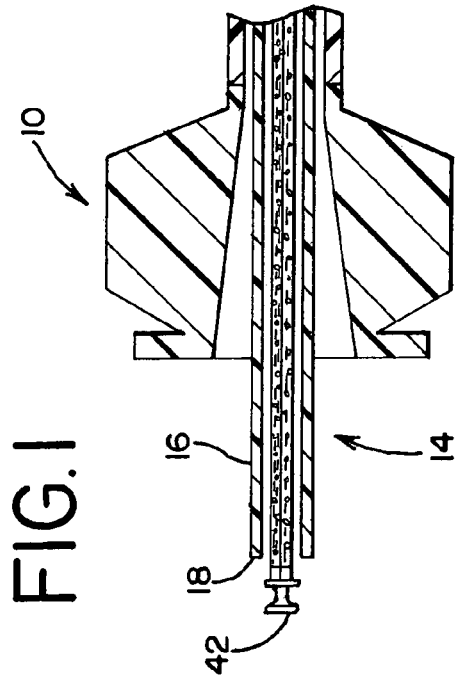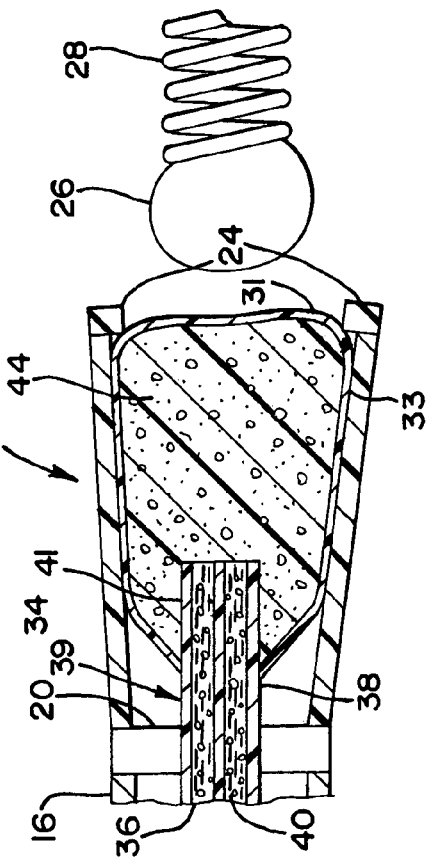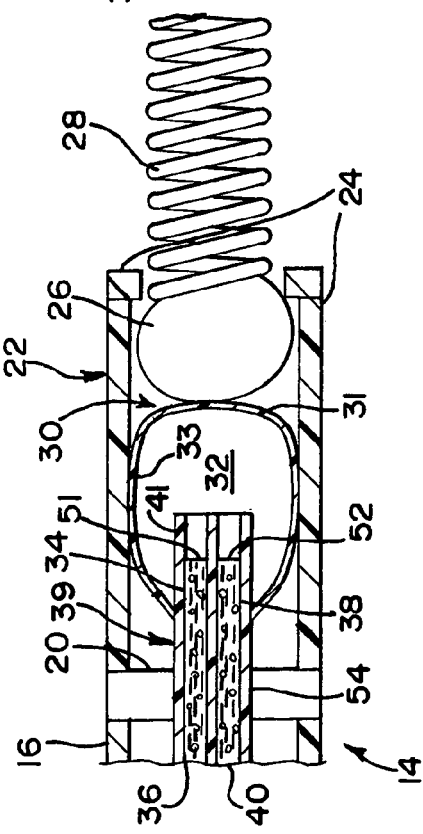
FIG.1
FIG.2
FIG.3

CHEMICALLY BASED VASCULAR OCCLUSION DEVICE DEPLOYMENT WITH GRIPPING FEATURE

FIELD OF THE INVENTION

The present invention is related to deployment systems and methods for accurately and rapidly deploying vascular occlusion devices at a preselected location within the vascular system of a patient, and more particularly, deployment approaches that utilize a pusher having an expandable gripper which is opened by the action of an expandable chemical reaction chamber to facilitate rapid deployment of vascular occlusion devices.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat such a defect. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has been delivered by the catheter and provides a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that interfere with other surgical and/or monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transmits the light into heat energy. The heat energy raises the temperature of the connector and opens the fingers, thereby releasing the embolic coil. This delivery system and the other above-identified delivery systems require electronic equipment powered by a power source. If the electronic equipment is defective or the power source fails, for example a battery pack fails, the procedure may be prolonged while the equipment is repaired or replaced. Prolonging the procedure may expose the patient to additional risk. This patent, and all other patents and references identified herein are hereby incorporated herein by reference.

Therefore, a need remains for a rapid release vascular occlusion deployment system or method that does not rely on electrical equipment or a power supply, is simple to manufacture, flexible and easy to guide through the vasculature of the body, provides better control over the occlusion device, and reduces the possibility of interference with other surgical and/or monitoring equipment.

SUMMARY OF INVENTION

The present invention embodies deployment systems and methods for accurately and rapidly deploying a vascular occlusion device at a preselected site within the vasculature of a patient. The deployment system may employ an elongated flexible delivery catheter for guiding a deployment unit to the preselected site. The deployment unit includes a pusher which has a gripper located at a distal end portion of the pusher. The gripper has an expandable gripping element, for example a plurality of gripping jaws, for releasably attaching a vascular occlusion device, such as an embolic coil, to the deployment system. The pusher guides the vascular occlusion device through the delivery catheter to the preselected site.

An expandable reaction chamber operatively communicates with the gripper. The delivery system also includes a first dispensing unit for dispensing a first reactant into the reaction chamber and a second dispensing unit for dispensing a second reactant into the reaction chamber. When the first and second reactants are dispensed into the chamber, they react to form a product that has a larger volume than the combined volumes of the first and second reactants prior to reacting. The product pushes against the inner wall of the expandable reaction chamber which causes the reaction chamber to outwardly expand. As the reaction chamber expands, it pushes against the gripping element causing the gripping element to outwardly expand or open so that the gripping element releases the vascular occlusion device, thereby deploying the vascular occlusion device at the preselected location.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is an enlarged, partially sectioned view of the vascular occlusion device deployment system of a preferred embodiment of the present invention;

FIG. 2 is an enlarged partially sectioned view showing the deployment unit of FIG. 1 prior to deployment of the occlusion device;

FIG. 3 is an enlarged partially sectioned view of the deployment unit of FIG. 2 shown just after deployment of the vascular occlusion device;

DESCRIPTION OF THE PREFERRED EMBODIMENTS

Figure 4:
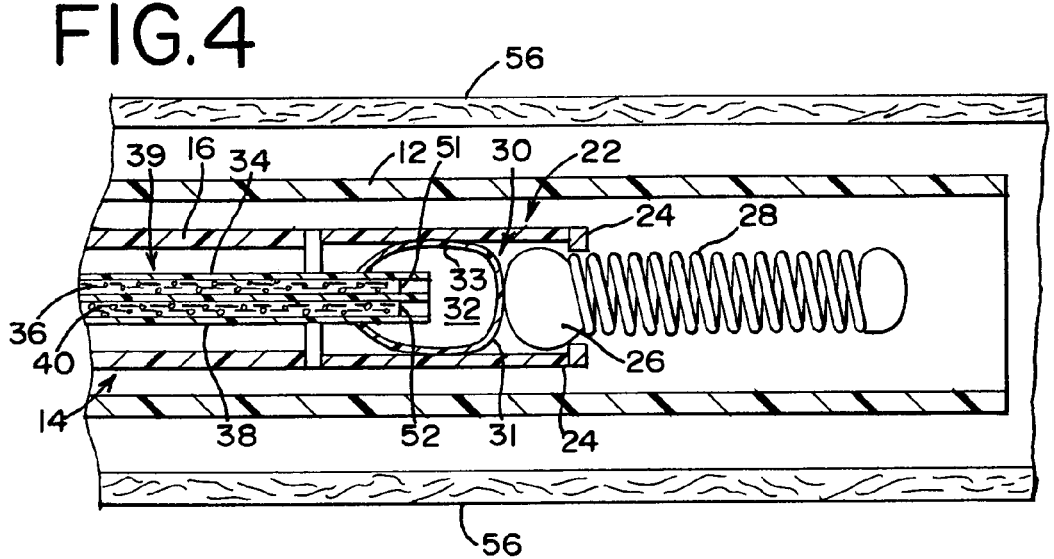
FIG. 4 is an enlarged partially sectioned view of the deployment system of FIG. 1 positioned at a preselected location within the vasculature system of a patient.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the vascular occlusion device deployment system of the present invention. The deployment system, generally designated at 10, includes an elongated flexible guiding catheter 12 which is inserted into the vascular system of a patient and used to guide a deployment unit, generally designed 14, to a preselected site in a manner generally known in the art. The deployment system 14 includes an elongated flexible pusher or delivery tube 16 having a proximal end portion 18 and a distal end portion 20.

As best illustrated in FIG. 2, a gripper 22 is located at the distal end portion 20 of the pusher 16. The gripper 22 includes an outwardly expandable gripping element 24, which is generally illustrated as a plurality of jaws. The gripping element 24 releasably engages a protruding portion or headpiece 26 of a vascular occlusion device 28, such as an embolic coil. As will be discussed in more detail below, when the gripping element expands outwardly, it releases the headpiece 26 of the vascular occlusion device 28.

The gripper 22 may be comprised of polymer, such as FEP Teflon, PTFE Teflon, polyvinyl chloride, a polyolefin or a neoprene, or any other suitable polymer, and may be constructed as disclosed in Bennett et al. U.S. Pat. No. 5,609,608, hereby incorporated herein by reference. Alternatively, the gripper 22 may be constructed of any suitable metal, or the gripper could comprise a microtube which has been slit. A suitable microtube may be made of stainless steel or of a nickel-titanium alloy such as Nitinol, or other suitable material. Further, in the illustrated embodiment, the gripper 22 is a separated unit which is attached to the pusher 16 in any suitable manner, for example by a silicone or cyanoacrylate adhesive. However, it is also contemplated that the gripper 22 and pusher 16 could be a unitary structure.

As stated above, the occlusion device 28 may be an embolic coil which may take various forms and configurations, and may also be filled with a fibrous material or may be coated with a beneficial substance, such as a biogel to promote clotting. Alternatively, the occlusion device also may be any other occlusion device or approach known in the art such as hydrogels, foams, bioactive coils, braids, cables, and hybrid devices.

An expandable reaction chamber 30 is positioned within the gripper 22. The reaction chamber 30, which for illustrative purposes is depicted as a microballoon, is preferably comprised of an elastic membrane 31. The elastic membrane may be constructed from materials that do not significantly degrade while in contact with the reactant materials or the product formed therefrom. Typically, these will be an elastic polymer, such as silicone, a polyamide, a nylon, or a polyolefin such as polyethylene. The reaction chamber 30 includes a cavity 32 defined by the inner surface 33 of the membrane 31.

The delivery unit 14 also includes a first dispensing unit 34 for dispensing a first reactant 36 into the cavity 32 of the reaction chamber 30 and a second dispensing unit 38 for dispensing a second reactant 40 into the cavity 32 of the reaction chamber 30. For illustrative purposes, the dispensing units 34 and 38 comprise a dual-lumen, plunger-activated dispensing tube 39 which extends within the pusher 16 from the proximal end portion 18 to the distal end portion 20 of the pusher 16. A distal end portion 41 of the dual lumen dispensing tube 39 may extend through the membrane 31 of the reaction chamber 30 into the cavity 32. The membrane 31 and dispensing tube 39 may be attached and sealed together by an adhesive, such as a silicone or cyanoacrylate adhesive. Alternatively, the membrane 31 may be wrapped around the dispensing tube 39 and attached and sealed with a similar adhesive. Other connection approaches can be practiced, such as those incorporating shrink tubing or other connector members.

The reactants 36, 40 may be dispensed from the lumens to the cavity 30 by activating a plunger 42 (which can be seen in FIG. 1) located at a proximal end portion of the dispensing tube 39. Typically, the reactants, prior to dispensing them, are secured within the respective lumens by a breakable seal 51, 52, respectively. Such seals should be selected to be made of a material that does not significantly degrade while in contact with the reactant materials. In addition, a fluid pressure release feature can be included to prevent the build up of fluid pressure within the reaction chamber when dispensing the reactants. This may take the form of a vent lumen 54 (FIG. 2).

As illustrated in FIG. 3, when the first and second reactants 36, 40 are dispensed into the cavity 32, they are mixed to produce a product 44 which has a greater volume than the combined volume of the first and second reactants prior to mixing. The expanding product 44 pushes against the inner surface 33 of the membrane 31, causing the membrane 31 to outwardly expand. The force of the expanded membrane 31 against the gripping element 24 forces the gripping element to outwardly expand or open. Movement in this regard can be in a generally radial direction. Additionally, the expanding membrane 31 also may contact the headpiece 26 of the occlusion device 28 and push the headpiece 26 out of and away from the expanded gripping element 24, when this action is desired.

The first and second reactants 36, 40 can be any reactants that produce a product 44 having a greater volume than the original compositions. Preferably, the first and second reactants may be any of the reactants disclosed in Cooke et al. WO 92/09651, hereby incorporated herein by reference, which produce a polycyanoacrylate foam. In particular, the first reactant is preferably a mixture of cyanoacrylate monomer and ethanol and the second reactant is preferably a mixture of ethanol and N,N-Dimethyl-p-toluidine. Other reactant materials, that when combined form a foam material with an increased bulk volume relative to the reactants, such as precursors for polyurethane foam, are also suitable.

Figure 5:
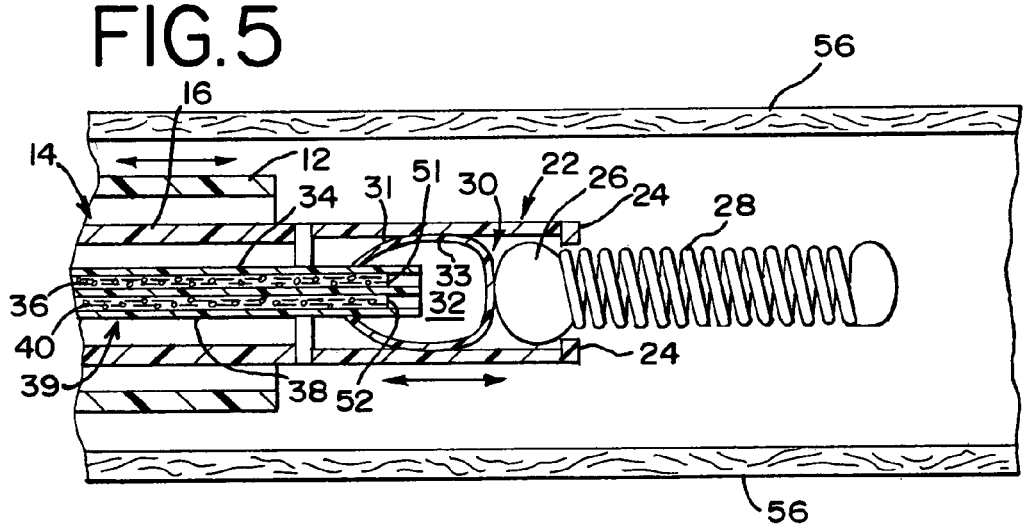
FIG. 5 is an enlarged partially sectioned view of the deployment system of FIG. 1 positioned at a preselected location within the vasculature system of a patient with the vascular occlusion device extending out of the distal end of the delivery catheter.
Figure 6:
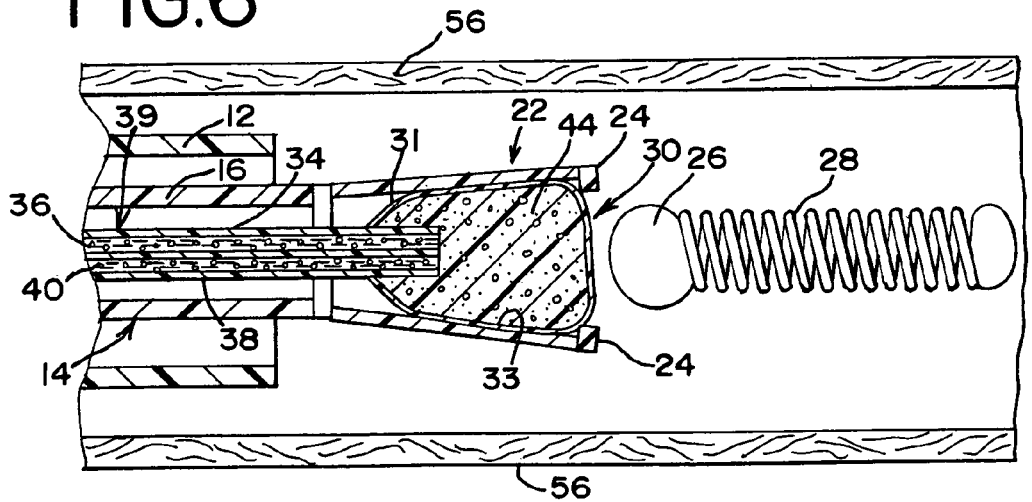
FIG. 6 is an enlarged partially sectioned view of the deployment system of FIG. 1 shown just after the vascular occlusion device has been deployed at a preselected location within the vasculature system of a patient.

As illustrated in FIGS. 4-6, in operation, the catheter 12 is inserted into the vasculature system of a patient and positioned at a preselected location within a blood vessel 56, typically in conjunction with other devices and professional procedures as generally known in the art. The delivery unit 14 is inserted into the catheter 12, and as shown in FIG. 5, once the desired location is reached, the delivery unit 14 is advanced, and/or the catheter 12 is moved in a retrograde manner, such that the delivery unit moves with respect to and within the catheter until the occlusion device 28 moves through the catheter 12 and out of the distal end of the catheter. During the procedure and before the occlusion device 28 has been deployed, if it is determined that the distal end of the catheter 12 or the occlusion device 28 is not in the correct location, the occlusion device may be retrieved back into the distal end of the catheter by retracting the delivery unit 14 proximally or advancing the catheter distally. Once the occlusion device has been retrieved, the catheter and/or the occlusion device may be repositioned.

When the occlusion device 28 is in the correct position, the plunger 42 may be activated to dispense the first and second reactants 36, 40 into the cavity 32 of the reaction chamber 30. As illustrated in FIG. 6, the first and second reactants 36, 40 mix within the cavity 32 and react to form a product 44 which has a larger volume than the combined volumes of the first and second reactants prior to mixing. The expanding product 44 pushes against the inner wall 33 of the membrane 31 of the reaction chamber 30, causing the membrane 31 to expand. The expanded membrane 31 presses against the gripping element 24 outwardly expanding or opening the gripping element to release the occlusion device 28 at the preselected location within the blood vessel 56. If desired, the membrane 31 may simultaneously press against the headpiece 26 to push it out of and away from the gripping element 24, thereby deploying the vascular occlusion device 28.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion device deployment system, comprising:
   a vascular occlusion device having a protruding portion;
   a deployment unit comprising a pusher having a proximal end portion and a distal end portion;
   an expandable gripper located at the distal end portion of the pusher, said gripper including an outwardly expandable gripping element for gripping the protruding portion of the vascular occlusion device;
   a dispensing tube adapted to accommodate a first reactant separate from a second reactant;
   an expandable reaction chamber located within said gripper, said expandable reaction chamber having an expandable interior cavity accessible through an opening, said dispensing tube being fluid in communication with said opening into the expandable reaction chamber; and
   said chamber expands upon a reaction of at least said first reactant and said second reactant within said closed interior cavity of said chamber whereby the expansion of the chamber causes the gripper to outwardly expand, releasing the protruding portion of the vascular occlusion device.

2. The deployment system of claim 1 wherein the expandable reaction chamber comprises a polymeric material.

3. The deployment system of claim 1 wherein the gripping elements comprise a plurality of jaws.

4. The deployment system of claim 1 wherein the first reactant comprises a mixture of cyanoacrylate monomer and ethanol, and the second reactant comprises a mixture of ethanol and N,N-Dirnethyl-p-toluidine.

5. The deployment system of claim 1 wherein the first and second reactants produce a polycyanoacrylate foam when mixed together.

6. The deployment system of claim 1 wherein said dispensing tube includes a first dispensing unit for dispensing the first reactant into the cavity of said expandable reaction chamber, and a second dispensing unit for dispensing the second reactant into the cavity of the reaction chamber.

7. The deployment system of claim 1 wherein the first dispensing unit comprises a first lumen and the second dispensing unit comprises a second lumen.

8. The deployment system of claim 7 wherein the first and second lumens extend through the pusher.

9. The deployment system of claim 7 wherein the first lumen and the second lumen comprise said dispensing tube which is a dual lumen dispensing unit.

10. The deployment system of claim 7 wherein the first lumen and the second lumen are plunger operated.

11. A vascular occlusion device deployment system for deploying a vascular occlusion device at a preselected site within the vasculature of a patient, comprising:
    a deployment unit comprising a pusher having a proximal end portion and a distal end portion;

an expandable gripper located at the distal end portion of the pusher, said gripper including an outwardly expandable gripping element for gripping a vascular occlusion device;

an expandable reaction chamber located for engagement with said gripper, said reaction chamber having an expandable interior cavity that has a first volume and a second volume that is greater than said first volume;

a first dispensing unit including a first reactant, said first dispensing unit opening into the expandable reaction chamber;

a second dispensing unit including a second reactant, said second dispensing unit opening into the expandable reaction chamber; and said expandable reaction chamber receives the first reactant from said first dispensing unit and the second reactant from said second dispensing unit to produce a product within the expandable reaction chamber that has a volume larger than the combined volume of said first and second reactants prior to mixing, said larger volume of the product causing the expandable reaction chamber to expand outwardly to said second volume and cause the gripping element to expand outwardly for releasing the vascular occlusion device therefrom.

12. The deployment system of claim 11 wherein the expandable reaction chamber comprises an elastomeric polymer material.

13. The deployment system of claim 11 wherein the gripper element comprises a plurality of expandable jaws.

14. The deployment system of claim 11 wherein the first reactant comprises a mixture of cyanoacrylate monomer and ethanol, and the second reactant comprises a mixture of ethanol and N,N-Dimethyl-p-toluidine.

15. The deployment system of claim 11 wherein the first and second reactants produce a polycyanoacrylate foam when mixed together.

16. The deployment system of claim 11 wherein the first dispensing unit comprises a first a lumen having said first reactant therein and the second dispensing unit comprises a second lumen having said second reactant therein.

17. The deployment system of claim 16 wherein the first and second lumens extend through the pusher.

18. A method for deployment of a vascular occlusion device at a preselected location within the vasculature of a patient, comprising:

providing a deployment unit comprising a pusher member having a gripper located at a distal end of the pusher member, said gripper having an expandable gripper element for gripping a vascular occlusion device and an expandable reaction chamber disposed within said gripper;

gripping a protruding portion of a vascular occlusion device with said gripper;

guiding the vascular occlusion device to a preselected location with in the vasculature of a patient with said pusher;

mixing at least a first reactant and a second reactant within the interior of the expandable reaction chamber to provide a product having a volume greater than the combined volume of the first and second reactants, said product expanding the expandable reaction chamber; and expanding the gripping elements under the force of the expanding reaction chamber, thereby releasing the protruding portion of the vascular occlusion device.

19. The method of claim 18 further including pushing the coil out of the gripper under the force of the expanding reaction chamber.

20. The method of claim 18 wherein the mixing of at least said first reactant and said second reactant comprises dispensing a first reactant into the cavity through a first dispensing lumen and dispensing the second reactant into the cavity through a second dispensing lumen.

21. The method of claim 18 wherein the mixing of at least said first reactant and said second reactant comprises mixing a cyanoacrylate monomer and ethanol, and a mixture of ethanol and N,N-Dimethyl-p-toluidine.

* * * * *